(12) United States Patent
Cottard et al.

(10) Patent No.: US 7,559,957 B2
(45) Date of Patent: Jul. 14, 2009

(54) DYEING COMPOSITION COMPRISING AT LEAST ONE OXIDATION DYE AND AT LEAST ONE POLYMER COMPRISING AN ACRYLAMIDE, DIALKYLDIALLYLAMMONIUM HALIDE AND VINYLCARBOXYLIC ACID, WITH A HIGH CONTENT OF ACRYLAMIDE

(75) Inventors: François Cottard, Courbevoie (FR); Gautier Deconinck, Saint-Gratien (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/889,239

(22) Filed: Aug. 10, 2007

(65) Prior Publication Data

US 2008/0066772 A1   Mar. 20, 2008

Related U.S. Application Data

(60) Provisional application No. 60/841,238, filed on Aug. 31, 2006.

(30) Foreign Application Priority Data

Aug. 10, 2006   (FR) .................................. 06 07244

(51) Int. Cl.
*A61Q 5/10*   (2006.01)
(52) U.S. Cl. ..................... 8/405; 8/406; 8/409; 8/410; 8/421; 8/435; 8/552; 8/554; 8/555; 8/558
(58) Field of Classification Search .................... 8/405, 8/406, 409, 410, 421, 435, 552, 554, 555, 8/558
See application file for complete search history.

(56) References Cited

U.S. PATENT DOCUMENTS

| | | | |
|---|---|---|---|
| 4,003,699 A | 1/1977 | Rose et al. | |
| 4,823,985 A | 4/1989 | Grollier et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,766,576 A | 6/1998 | Löwe et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 2002/0050013 A1 | 5/2002 | Vidal et al. | |
| 2003/0019051 A9 | 1/2003 | Vidal et al. | |
| 2004/0060126 A1* | 4/2004 | Cottard et al. .................. | 8/405 |
| 2004/0133996 A1 | 7/2004 | Wolff et al. | |
| 2005/0015895 A1 | 1/2005 | Azizova et al. | |

| | | |
|---|---|---|
| 2008/0034507 A1 | 2/2008 | Cottard et al. |

FOREIGN PATENT DOCUMENTS

| | | |
|---|---|---|
| DE | 23 59 399 A1 | 6/1975 |
| DE | 38 43 892 A1 | 6/1990 |
| DE | 41 33 957 A1 | 4/1993 |
| DE | 195 43 988 A1 | 5/1997 |
| EP | 0 521 665 | 1/1993 |
| EP | 0 522 755 A1 | 1/1993 |
| EP | 1 048 290 A2 | 11/2000 |
| FR | 2 586 913 A1 | 3/1987 |
| FR | 2 733 749 A1 | 11/1996 |
| FR | 2 750 048 A1 | 12/1997 |
| FR | 2 817 467 A1 | 6/2002 |
| GB | 1 026 978 | 4/1966 |
| GB | 1 153 196 | 5/1969 |
| JP | 2-19576 | 1/1990 |
| JP | 9-110659 | 4/1997 |
| WO | WO 94/06403 | 3/1994 |
| WO | WO 94/08969 | 4/1994 |
| WO | WO 94/08970 | 4/1994 |
| WO | WO 96/15765 | 5/1996 |
| WO | WO 02/45674 | 6/2002 |

OTHER PUBLICATIONS

Product Bulletin PC-PolyQ-39.*

(Continued)

*Primary Examiner*—Eisa B Elhilo
(74) *Attorney, Agent, or Firm*—Finnegan, Henderson, Farabow, Garrett & Dunner

(57) ABSTRACT

Disclosed herein is a composition for the oxidation dyeing of keratin fibers, for example, human keratin fibers such as the hair, comprising, in a medium that is suitable for dyeing, at least one oxidation dye and at least one polymer comprising a repetition of: (i) from 45 mol % to 60 mol % of at least one unit derived from a monomer of acrylamide type, (ii) at least one unit derived from a monomer of dialkyldiallylammonium halide type, and (iii) at least one unit derived from a monomer of vinylcarboxylic acid type, wherein the mole ratio of the amount of the at least one unit derived from a monomer of dialkyldiallylammonium halide type to the amount of the at least one unit derived from a monomer of vinylcarboxylic acid type is greater than or equal to 1. The composition disclosed herein makes it possible to prevent or reduce the phenomenon of static electricity at the surface of the hair, while at the same time maintaining good rheological and dyeing properties.

23 Claims, No Drawings

OTHER PUBLICATIONS

French Search Report for FR 0607244, dated Mar. 13, 2007.
English language abstract of JP 2-19576, Jan. 23, 1990.
English language abstract of JP 9-110659, Apr. 28, 1997.
Declaration Under 37 C.F.R. 1.132 executed by G. Deconinck on Jan. 15, 2009, as-filed in co-pending U.S. Appl. No. 11/889,243 on Feb. 13, 2009, 6 pages.
French Search Report issued in FR 06/07247, dated Mar. 27, 2007, cited in co-pending U.S. Appl. No. 11/889,243, 2 pages.
Aug. 13, 2008 Office Action issued in co-pending U.S. Appl. No. 11/889,243, 7 pages.
Response to Aug. 13, 2008 Office Action as-filed in co-pending U.S. Appl. No. 11/889,243 on Feb. 13, 2009, 5 pages.

* cited by examiner

DYEING COMPOSITION COMPRISING AT LEAST ONE OXIDATION DYE AND AT LEAST ONE POLYMER COMPRISING AN ACRYLAMIDE, DIALKYLDIALLYLAMMONIUM HALIDE AND VINYLCARBOXYLIC ACID, WITH A HIGH CONTENT OF ACRYLAMIDE

This application claims benefit of U.S. Provisional Application No. 60/841,238, filed Aug. 31, 2006, the contents of which are incorporated herein by reference. This application also claims benefit of priority under 35 U.S.C. § 119 to French Patent Application No. FR 06/07244, filed Aug. 10, 2006, the contents of which are also incorporated herein by reference.

Disclosed herein is a composition for the oxidation dyeing of keratin fibers, for example, of human keratin fibers such as the hair, comprising, in a medium that is suitable for dyeing, at least one oxidation dye and at least one particular amphoteric polymer described below.

It is known practice to dye keratin fibers such as human hair with dyeing compositions containing oxidation dyes, such as oxidation dye precursors and coloration modifiers.

Oxidation dye precursors, which are known as oxidation bases, are compounds that are initially colorless or weakly colored, which, when combined with oxidizing products, may give rise to colored compounds and dyes via a process of oxidative condensation. They may be, for example, compounds such as ortho- or para-phenylenediamines, ortho- or para-aminophenols and heterocyclic bases.

It is also known that the shades obtained with these oxidation bases may be varied by combining them with couplers or coloration modifiers, the latter being chosen, for example, from meta-diaminobenzenes, meta-aminophenols, meta-diphenols and certain heterocyclic compounds such as indole compounds.

The variety of molecules used as oxidation bases and couplers allows a wide range of colors to be obtained.

The "permanent" coloration obtained by virtue of these oxidation dyes, which is also known as oxidation dyeing, should moreover satisfy certain criteria. For example, it should not have toxicological drawbacks, it should be able to produce shades in the desired intensity and it should show good resistance to external agents such as light, bad weather, washing, permanent-waving, perspiration and rubbing.

The dyes should also allow grey hair to be covered and, finally, they should be as unselective as possible, i.e. they should produce the smallest possible coloration differences along the same keratin fiber, which may be differently sensitized (i.e. damaged) between its end and its root.

European Patent Application No. EP 1 048 290 describes a composition for the oxidation dyeing of the hair, comprising an oxidation dye precursor, a coupler and an amphoteric polymer comprising repeating units (a) of acrylic acid and (b) of a cationic monomer chosen from methacrylamidopropyl-trimethylammonium chloride and dimethyldiallylammonium chloride, and mixtures thereof, the molar ratio between the units (a) and the units (b) being greater than or equal to ⅓. This composition can make it possible to improve the deposition of the dyes on the hair and thus render the dyeing more effective.

United States Patent Application Publication No. 2005/0015895 describes a composition for the oxidation dyeing of the hair, comprising an oxidation dye and a quaternary amphoteric terpolymer comprising the following repeating units: (a) methacrylamidopropyltrimethylammonium chloride or dimethyldiallylammonium chloride, (b) acrylic acid or sodium methacrylate, and (c) acrylamide, with a ratio (a)/(b) of greater than or equal to 4. This composition can make it possible to produce a better conditioning effect on hair fibers.

Finally, French Patent No. FR 2 817 467 describes a composition for the oxidation dyeing of keratin fibers, comprising an oxidation dye, an associative polymer and a polymer containing units derived from a monomer of (i) acrylamide, (ii) dialkyldiallylammonium halide, and (iii) vinylcarboxylic acid type. This composition can allow for optimum application on the fibers, for example does not run, without, however, impairing the coloring qualities.

However, the oxidation dyeing compositions of the prior art have certain drawbacks. For instance, their use is liable to lead to the phenomenon of static electricity at the surface of the keratin fibers, or of increasing such a phenomenon.

Accordingly, there is a heed in the art for novel compositions for the oxidation dyeing of keratin fibers, that do not have the drawbacks of the prior art. Thus, the present disclosure relates to oxidation dyeing compositions that can reduce the phenomenon of static electricity after dyeing.

Accordingly, disclosed herein is a composition for the oxidation dyeing of keratin fibers, for example, human keratin fibers such as the hair, comprising, in a medium that is suitable for dyeing, at least one oxidation dye and at least one amphoteric polymer comprising a repetition of:

(i) from 45 mol % to 60 mol % of at least one unit derived from a monomer of acrylamide type, (ii) at least one unit derived from a monomer of dialkyldiallylammonium halide type, and (iii) at least one unit derived from a monomer of vinylcarboxylic acid type, wherein the mole ratio of the amount of the at least one unit derived from a monomer of dialkyldiallylammonium halide type to the amount of the at least one unit derived from a monomer of vinylcarboxylic acid type of greater than or equal to 1.

The composition disclosed herein can make it possible to prevent or reduce the phenomenon of static electricity at the surface of the hair, while at the same time maintaining good rheological properties. In addition, it can make it possible to improve the cosmetic properties of the hair, such as disentangling and smoothing.

Finally, the dyeing properties of this composition can be very satisfactory, as regards both the selectivity and the intensity of the coloration obtained.

The present disclosure also relates to a process for dyeing keratin fibers, in which a composition as disclosed herein is applied to the keratin fibers, in the presence of at least one oxidizing agent, for a time that is sufficient to develop the desired coloration.

The present disclosure also relates to a multi-compartment device for the implementation of the process disclosed herein.

The present disclosure still further relates to the use of the composition disclosed herein for the oxidation dyeing of keratin fibers.

Finally, the present disclosure relates to the use, in an oxidation dyeing composition, of at least one amphoteric polymer as disclosed herein, in order to prevent or reduce the phenomenon of static electricity at the surface of the hair.

Unless otherwise indicated, the limits of the ranges of values that are given in the context of the present disclosure are included in these ranges.

According to at least one embodiment, the at least one unit derived from a monomer of acrylamide type of the amphoteric polymer that is useful in the context of the present disclosure can be chosen from units of formula (I):

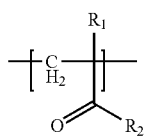

(I)

in which:

R$_1$ is H or CH$_3$, and

R$_2$ is chosen from amino, dimethylamino, tert-butylamino, dodecylamino and —NH—CH$_2$OH radicals.

According to at least one embodiment of the present disclosure, the at least one amphoteric polymer of the present disclosure comprises a repetition of one single unit of formula (I).

According to another embodiment of the present disclosure, the at least one unit derived from a monomer of acrylamide type chosen from units of formula (I), in which R$_1$ denotes H and R$_2$ is an amino radical, i.e. corresponding to the acrylamide monomer, can be used.

According to at least one embodiment of the present disclosure, the at least one unit derived from a monomer of dialkyldiallylammonium halide type of the amphoteric polymer can be chosen from those of formula (II):

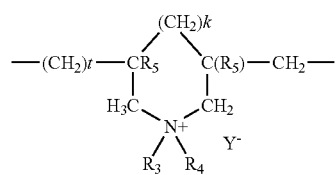

(II)

in which:

k and t are equal to 0 or 1, the sum k+t being equal to 1;

R$_5$ is H or CH$_3$;

R$_3$ and R$_4$, independently of each other, are chosen from C$_1$-C$_4$ alkyl groups, C$_1$-C$_5$ hydroxyalkyl groups, and amido(C$_1$-C$_4$)alkyl groups, or R$_3$ and R$_4$ may form, together with the nitrogen atom to which they are attached, heterocyclic groups such as piperidyl or morpholinyl; for example R$_3$ and R$_4$, independently of each other, can be chosen from, C$_1$-C$_4$ alkyl groups;

Y$^-$ is chosen from anions such as bromide, chloride, acetate, borate, citrate, tartrate, bisulfate, bisulfite, sulfate and phosphate.

According to at least one embodiment of the present disclosure, the at least one unit derived from a monomer of dialkyldiallylammonium halide type, includes those for which R$_5$ is H, R$_3$ and R$_4$ are methyl radicals, and Y$^-$ is a chloride anion.

According to at least one embodiment of the present disclosure, the at least one unit derived from a monomer of vinylcarboxylic acid type of the amphoteric polymer can be chosen from the units of formula (III):

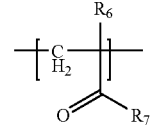

(III)

in which:

R$_6$ is H or CH$_3$, and

R$_7$ is a hydroxyl radical or a radical —NH—C(CH$_3$)$_2$—CH$_2$—SO$_3$H.

For example, the at least one unit derived from a monomer of vinylcarboxylic acid type may be chosen from acrylic acid, methacrylic acid and 2-acrylamido-2-methylpropanesulfonic acid monomers.

According to still another embodiment, the at least one unit derived from a monomer of vinylcarboxylic acid type can be acrylic acid, for which R$_6$ is H and R$_7$ is a hydroxyl radical.

As disclosed herein, the at least one amphoteric polymer comprises from 45 mol % to 60 mol % of at least one unit derived from a monomer of acrylamide type, for example, from 45 mol % to 55 mol % of at least one unit derived from a monomer of acrylamide type.

According to at least one embodiment, the said at least one amphoteric polymer comprises 30 mol % or less of at least one unit derived from a monomer of vinylcarboxylic acid type.

According to at least one embodiment, the at least one amphoteric polymer comprises from 5 mol % to 30 mol % and for example, from 15 mol % to 25 mol % of at least one unit derived from a monomer of vinylcarboxylic acid type.

Finally, the mole ratio of the amount of the at least one unit derived from a monomer of dialkyldiallylammonium halide type to the amount of the at least one unit derived from a monomer of vinylcarboxylic acid type should be greater than or equal to 1. In at least one embodiement, this ratio ranges from 1 to 2, for instance, from 1 to 1.5, for example, from 1.1 to 1.3.

The at least one amphoteric polymer may comprise at least 25 mol %, for example, from 25 mol % to 30 mol % of at least one unit derived from a monomer of dialkyldiallylammonium halide type.

The at least one amphoteric polymer disclosed herein may also comprise additional units, other than the units derived from a monomer of acrylamide, dialkyldiallylammonium halide and vinylcarboxylic acid type, provided that it comprises from 45 mol % to 60 mol % of at least one unit derived from a monomer of acrylamide type, and provided the mole ratio of the amount of the at least one unit derived from a monomer of dialkyldiallylammonium halide type to the amount of the at least one unit derived from a monomer of vinylcarboxylic acid type, is greater than or equal to 1.

As examples of polymers containing units derived from monomers of (i) acrylamide, (ii) dialkyldiallylammonium halide, and (iii) vinylcarboxylic acid type, non-limiting mention may be made of acrylamide/dimethyldiallylammonium chloride/acrylic acid terpolymers, which are listed in the CTFA International Cosmetic Ingredient Dictionary, 10th edition 2004, under the name "Polyquaternium-39". The polymers according to the disclosure may thus be chosen from Polyquaterniums-39 containing from 45 mol % to 60 mol % of at least one unit derived from acrylamide, and having a mole ratio of the amount of the at least one unit derived from dimethyldiallylammonium chloride to the amount of the at least one unit derived from acrylic acid of greater than or equal to 1, for instance the product sold under the name Merquat 3331 by the company Nalco.

The at least one amphoteric polymer according to the present disclosure may be prepared in a conventional manner, by polymerization of its various monomers, according to techniques known to those skilled in the art, and for example by free-radical polymerization.

The at least one amphoteric polymer useful in the context of the present disclosure can be, according to at least one embodiment, present in an amount ranging from 0.1% to 10% by weight, such as from 0.5% to 5% by weight, for instance, from 1% to 4% by weight relative to the total weight of the composition.

The composition disclosed herein comprises at least one oxidation dye that may be chosen from oxidation bases and couplers.

The oxidation bases that may be used in the context of the present disclosure are chosen from those conventionally known in oxidation dyeing, such as ortho- and para-phenylenediamines, double bases, ortho- and para-aminophenols and heterocyclic bases, and also the acid addition salts thereof.

The para-phenylenediamines that may be used in the context of the present disclosure may be chosen, for example, from the compounds of formula (IV) below, and the acid addition salts thereof:

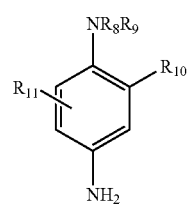

(IV)

in which:

$R_8$ is chosen from hydrogen, $C_1$-$C_4$ alkyl radicals, $C_1$-$C_4$ monohydroxyalkyl radicals, $C_2$-$C_4$ polyhydroxyalkyl radicals, ($C_1$-$C_4$)alkoxy($C_1$-$C_4$)alkyl radicals, $C_1$-$C_4$ alkyl radicals substituted with a nitrogenous radical, a phenyl radical and a 4'-aminophenyl radical;

$R_9$ is chosen from hydrogen, $C_1$-$C_4$ alkyl radicals, $C_1$-$C_4$ monohydroxyalkyl radicals, $C_2$-$C_4$ polyhydroxyalkyl radicals, ($C_1$-$C_4$)alkoxy($C_1$-$C_4$)alkyl radicals and $C_1$-$C_4$ alkyl radicals substituted with a nitrogenous radical;

$R_8$ and $R_9$ may also form with the nitrogen atom that bears them a 5- or 6-membered nitrogenous heterocycle optionally substituted with at least one entity chosen from alkyl, hydroxy and ureido groups;

$R_{10}$ is chosen from hydrogen, halogens such as chlorine, $C_1$-$C_4$ alkyl radicals, a sulfo radical, a carboxy radical, $C_1$-$C_4$ monohydroxyalkyl radicals, $C_1$-$C_4$ hydroxyalkoxy radicals, acetylamino($C_1$-$C_4$)alkoxy radicals, $C_1$-$C_4$ mesylaminoalkoxy radicals and carbamoylamino($C_1$-$C_4$)alkoxy radicals;

$R_{11}$ is chosen from hydrogen, halogens and $C_1$-$C_4$ alkyl radicals.

Among the nitrogenous groups of formula (IV) above, non-limiting mention may be made of amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium and ammonium radicals.

Among the para-phenylenediamines of formula (IV) above that may be mentioned are, by way of non-limiting example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxy-ethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine, and the acid addition salts thereof.

Further among the para-phenylenediamines of formula (IV) above that may be mentioned are, for instance, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the acid addition salts thereof.

According to the disclosure, the term "double bases" is understood to mean compounds containing at least two aromatic nuclei bearing amino and/or hydroxyl groups.

Among the double bases that may be used as oxidation bases in the composition in accordance with the disclosure, non-limiting mention may be made of the compounds of formula (V), and the acid addition salts thereof:

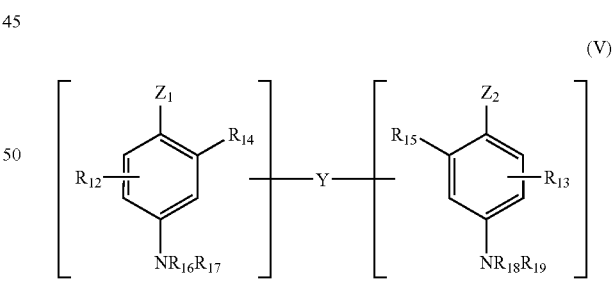

(V)

in which:

$Z_1$ and $Z_2$, which may be identical or different, can be a hydroxyl or —$NH_2$ group that may be substituted with a $C_1$-$C_4$ alkyl group or with a linker arm Y;

the linker arm Y is a linear or branched $C_1$-$C_{14}$ alkylene chain, which may be interrupted by or terminated with at least one nitrogenous group and/or at least one heteroatom such as oxygen, sulfur or nitrogen atom, and optionally substituted with at least one entity chosen from hydroxyl and $C_1$-$C_6$ alkoxy groups;

$R_{12}$ and $R_{13}$ are chosen from hydrogen, halogens, $C_1$-$C_4$ alkyl radicals, $C_1$-$C_4$ monohydroxyalkyl radicals, $C_2$-$C_4$ polyhydroxyalkyl radicals, $C_1$-$C_4$ aminoalkyl radicals and a linker arm Y;

$R_{14}$, $R_{15}$, $R_{16}$, $R_{17}$, $R_{18}$ and $R_{19}$, which may be identical or different, are chosen from hydrogen, a linker arm Y and $C_1$-$C_4$ alkyl radicals;

wherein the compounds of formula (V) contain only one linker arm Y per molecule.

Among the nitrogenous groups of formula (V) above, non-limiting mention may be made of amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium and ammonium radicals.

Among the double bases of formula (V) above, non-limiting mention may be made, for example, of N,N'-bis(β-hydroxyethyl)-N,N'-bis(4'-aminophenyl)-1,3-diamino-propanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the acid addition salts thereof.

In at least one embodiment, the double bases of formula (V), are chosen from, for example, N,N'-bis(β-hydroxyethyl)-N,N'-bis(4'-aminophenyl)-1,3-diaminopropanol and 1,8-bis(2,5-diaminophenoxy)-3,5-dioxaoctane, and the acid addition salts thereof.

In at least one embodiment of the present disclosure, the para-aminophenols can be chosen from the compounds of formula (VI), and the acid addition salts thereof:

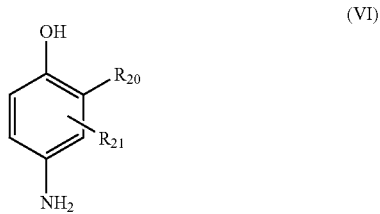

(VI)

in which:

$R_{20}$ is chosen from hydrogen, halogens such as fluorine, $C_1$-$C_4$ alkyl, $C_1$-$C_4$ monohydroxyalkyl, ($C_1$-$C_4$)alkoxy($C_1$-$C_4$)alkyl, $C_1$-$C_4$ aminoalkyl and hydroxy($C_1$-$C_4$)-alkylamino ($C_1$-$C_4$)alkyl groups, $R_{21}$ is chosen from hydrogen, halogens such as fluorine, $C_1$-$C_4$-alkyl, $C_1$-$C_4$ monohydroxyalkyl, $C_2$-$C_4$ polyhydroxyalkyl, $C_1$-$C_4$ aminoalkyl, $C_1$-$C_4$ cyanoalkyl and ($C_1$-$C_4$) alkoxy($C_1$-$C_4$)alkyl groups.

Among the para-aminophenols of formula (VI) above, non-limiting mention may be made, for example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the acid addition salts thereof.

In at least one embodiment of the present disclosure, the ortho-aminophenols may be chosen from, for instance, 2-aminophenol, 2-amino-1-hydroxy-5-methylbenzene, 2-amino-1-hydroxy-6-methylbenzene and 5-acetamido-2-aminophenol, and the acid addition salts thereof.

Among the heterocyclic bases which can be used as oxidation bases in the dyeing compositions disclosed herein, non-limiting mention may be made, for example, of pyridine derivatives, pyrimidine derivatives, pyrazole derivatives, and the acid addition salts thereof.

Among the pyridine derivatives, non-limiting mention may be made of the compounds described, for example, in British Patent Nos. GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Further among the pyrimidine derivatives, non-limiting mention may be made of the compounds described, for example, in German patent No. DE 2 359 399 or Japanese patents Nos. JP 88-169 571 and JP 91-10659 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French Patent Application No. FR-A-2 750 048 and among which mention may be made of, for instance, pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl) (2-hydroxyethyl)amino]ethanol; 2-[(7-aminopyrazolo[1,5-a]pyrimidin-3-yl) (2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine and 3-amino-5-methyl-7-imidazolylpropylaminopyrazolo[1,5-a]pyrimidine and the addition salts thereof and the tautomeric forms thereof, when a tautomeric equilibrium exists, and the acid addition salts thereof.

Among the pyrazole derivatives, non-limiting mention may be made of the compounds described, for example, in German Patent Nos. DE 3 843 892, DE 4 133 957 and the following patent applications: WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

The composition according to the present disclosure comprises a total amount of oxidation base ranging from 0.0005% to 12% by weight relative to the total weight of the composition. In at least one embodiment, it comprises a total amount of oxidation base(s) ranging from 0.005% to 8% by weight, such as from 0.05% to 5% by weight relative to the total weight of the said composition.

The at least one coupler according to the present disclosure may be chosen from those conventionally used in oxidation dyeing compositions, such as meta-aminophenols, meta-phenylenediamines and meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles and quinolines, and the acid addition salts thereof.

The at least one coupler may be chosen, for instance, from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, and the acid addition salts thereof.

The composition according to the present disclosure comprises a total amount of coupler ranging from 0.0001% to 15% by weight relative to the total weight of the composition. For example, it comprises a total amount of coupler ranging from 0.001% to 10% by weight and in at least one embodiment, from 0.01% to 8% by weight relative to the total weight of the composition.

The acid-addition salts of the oxidation bases and couplers can be chosen, for example, from the hydrochlorides, hydrobromides, sulfates, tartrates, lactates and acetates.

According to at least one embodiment of the present disclosure, the composition comprises at least one oxidation base and at least one coupler.

The dyeing composition in accordance with the present disclosure may also contain at least one direct dye that may be chosen, for example, from nitrobenzene dyes, azo direct dyes and methine direct dyes. These direct dyes may be of non-ionic, anionic or cationic nature.

The composition in accordance with the present disclosure may further comprise at least one oxidizing agent.

Such an oxidizing agent may be chosen, for example, from hydrogen peroxide, urea peroxide, alkali metal bromates or ferricyanides, and persalts such as perborates and persulfates.

In at least one embodiment, the at least one oxidizing agent is hydrogen peroxide. This oxidizing agent may consist, for example, of an aqueous hydrogen peroxide solution whose titre may vary, for example, from about 1 to 40 volumes and in at least one embodiment, from about 5 to 40 volumes.

At least one redox enzyme chosen from laccases, peroxidases and 2-electron oxidoreductases (such as uricase), optionally in the presence of the respective donor or cofactor thereof, may also be used as the at least one oxidizing agent.

The medium that is suitable for dyeing, also known as the dye support, may be a cosmetic medium comprising, for instance, water or of a mixture of water and of at least one cosmetically acceptable organic solvent. Non-limiting examples of organic solvents that may be mentioned include alcohols such as ethyl alcohol, isopropyl alcohol, benzyl alcohol and phenylethyl alcohol, or glycols or glycol ethers, for instance ethylene glycol monomethyl, monoethyl or monobutyl ether, propylene glycol or ethers thereof, for instance propylene glycol monomethyl ether, butylene glycol, dipropylene glycol and also diethylene glycol alkyl ethers, for instance diethylene glycol monoethyl ether or monobutyl ether. The at least one solvent can be present in an amount ranging from about 0.5% to 20%, for instance, from about 2% to 10% by weight relative to the total weight of the composition.

The composition in accordance with the present disclosure may also contain at least one adjuvant chosen from the various adjuvants conventionally used in hair dyeing compositions, such as anionic, cationic, nonionic, amphoteric or zwitterionic surfactants or mixtures thereof, anionic, cationic, nonionic, amphoteric or zwitterionic polymers or mixtures thereof, other than the amphoteric polymers disclosed herein, mineral or organic thickeners, such as anionic, cationic, nonionic and amphoteric polymeric associative thickeners, antioxidants, penetrants, sequestrants, fragrances, buffers, dispersants, conditioning agents, for instance volatile or nonvolatile, modified or unmodified silicones, film-forming agents, ceramides, preserving agents and opacifiers.

The above adjuvants may be present in an amount for each adjuvant ranging from 0.01% to 20% by weight relative to the weight of the dyeing composition.

Needless to say, a person skilled in the art will take care to select the optional additional compound(s) mentioned above, such that the beneficial properties intrinsically associated with the compositions according to the present disclosure are not, or are not substantially, adversely affected by the envisaged addition(s).

The pH of the composition in accordance with the present disclosure ranges from 3 to 12 approximately, for instance, from 5 to 11 approximately. It may be adjusted to the desired value using acidifying or basifying agents usually used in the dyeing of keratin fibers, or alternatively using standard buffer systems.

Among the basifying agents that may be mentioned, for example, non-limiting mention may be made of aqueous ammonia, alkali metal carbonates, alkanolamines such as monoethanolamine, diethanolamine and triethanolamine, and also derivatives thereof, oxyethylenated and/or oxypropylenated hydroxyalkylamines and ethylenediamines, sodium hydroxide, potassium hydroxide and compounds having the following formula:

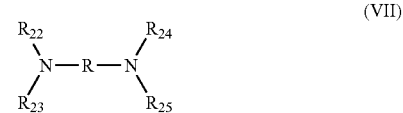

(VII)

in which R is a propylene residue optionally substituted with a hydroxyl group or a $C_1$-$C_4$ alkyl radical; $R_{22}$, $R_{23}$, $R_{24}$ and $R_{25}$, which may be identical or different, are chosen from hydrogen, $C_1$-$C_4$ alkyl, and $C_1$-$C_4$ hydroxyalkyl radicals.

Among the acidifying agents that may be mentioned, by way of non-limiting example, are mineral or organic acids, for instance hydrochloric acid, orthophosphoric acid, carboxylic acids, for instance tartaric acid, citric acid or lactic acid, or sulfonic acids.

The dyeing composition according to the present disclosure may be in various forms, such as in the form of liquids, creams or gels, or in any other form that is suitable for dyeing keratin fibers, such as human hair.

The process of the present disclosure is a process in which the composition as defined above is applied to the fibers, and the color is developed using at least one oxidizing agent. The color may be developed at acidic, neutral or alkaline pH. For instance, in at least one embodiment, the coloration is developed at neutral pH. The oxidizing, agent may be added to the composition of the present disclosure just at the time of use, or it may be used starting with an oxidizing composition containing it, which is applied simultaneously with or sequentially to the composition of the present disclosure.

According to at least one embodiment, the composition according to the present disclosure is mixed, for instance, at the time of use, with a composition containing, in a medium that is suitable for dyeing, at least one oxidizing agent, this oxidizing agent being present in an amount that is sufficient to develop a coloration. The mixture obtained is then applied to the keratin fibers. After a leave-on time ranging from 1 to 60 minutes approximately, for instance, from 5 to 45 minutes approximately, the keratin fibers are rinsed, washed with shampoo, rinsed again and then dried.

The present disclosure also relates to a multi-compartment device or dyeing "kit" in which at least one first compartment contains a dyeing composition as disclosed herein with the exception of the oxidizing agent, and at least one second compartment contains at least one oxidizing agent. This device may be equipped with an applicator to deposit the desired mixture to the hair, such as the devices described in French Patent No. FR-2 586 913.

The present disclosure also relates to the use for the oxidation dyeing of keratin fibers, for example, human keratin fibers such as the hair, of a dyeing composition as defined above.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

In these examples, all the amounts are indicated as weight percentages of active material (AM) relative to the total weight of the composition, unless otherwise indicated. Notwithstanding that the numerical ranges and parameters setting forth the broad scope of the present disclosure are approximations, the numerical values set forth in the specific example are reported as precisely as possible. Any numerical values, however, inherently contain certain errors necessarily resulting from the standard deviation found in their respective testing measurements.

The examples that follow are intended to illustrate the present disclosure without, however, limiting its scope.

EXAMPLES

Two dyeing compositions were prepared using the following compounds (comparative composition A and composition B according to the present disclosure):

| Composition | Composition A (Comparative) | Composition B (Inventive) |
|---|---|---|
| Lauryl alcohol oxyethylenated with 12 EO, sold under the name Rewopal 12 by the company Goldschmidt | 7.5 | 7.5 |
| Glycol monostearate | 2 | 2 |
| Oleocetyl alcohol oxyethylenated with 30 EO, sold under the name Emulgin O 30 by the company Cognis | 3 | 3 |
| Decyl alcohol oxyethylenated with 3 EO, sold under the name Emulgin BL 309 by the company Cognis | 10 | 10 |
| Cetylstearyl alcohol (50/50 C16/C18), sold under the name Lanette O OR by the company Cognis | 10 | 10 |
| Natural lauric acid | 2.5 | 2.5 |
| Hydrophobic fumed silica sold under the name Aerosil R972 by the company Degussa | 1 | 1 |
| Crosslinked polyacrylic acid sold under the name Carbopol 980 by the company Noveon | 0.4 | 0.4 |
| Propylene glycol | 10 | 10 |
| Monoethanolamine | 1.2 | 1.2 |
| Acrylamide/diallyldimethylammonium chloride/acrylic acid polymer (Merquat 3331 from Nalco) | — | 2.4 |
| Diethylenetriaminepentaacetic acid, pentasodium salt, as an aqueous 40% solution, sold under the name Dissolvine D40 by the company Akzo Nobel | 2 | 2 |
| Ammonium thiolactate as an aqueous 58% solution (50% thiolactic acid) | 0.8 | 0.8 |
| Ascorbic acid | 0.2 | 0.2 |
| Titanium dioxide | 0.2 | 0.2 |
| Aqueous ammonia containing 20% $NH_3$ | 10 | 10 |
| 2-Methyl-5-hydroxyethylaminophenol | 0.86 | 0.86 |
| p-Aminophenol | 0.41 | 0.41 |
| 4-Amino-2-hydroxytoluene | 0.57 | 0.57 |
| 6-Hydroxyindole | 0.068 | 0.068 |
| p-Phenylenediamine | 0.49 | 0.49 |
| Resorcinol | 0.1 | 0.1 |
| Fragrance | qs | qs |
| Water | qs 100 | qs 100 |

Each of the compositions A and B was mixed in a 1+1.5 weight ratio with an oxidizing composition having a hydrogen peroxide titre of 20 volumes.

The pHs of the mixtures thus obtained were 10.

These mixtures were applied to grey hair containing 90% white hairs, for a leave-on time of 30 minutes at room temperature.

The hair was then rinsed, washed with a standard shampoo, rinsed with water and then dried.

An aesthetic red shade with a coppery tint, which shows good fastness, was obtained with the mixtures derived from compositions A and B with the oxidizing composition.

It was observed that the mixture derived from composition B with the oxidizing composition generates less static electricity at the surface of the treated hair than that obtained with composition A.

In addition, after dyeing with the mixture derived from composition B, it was observed that the hair was particularly smooth.

What is claimed is:

1. A composition for the oxidation dyeing of keratin fibers, comprising, in a medium that is suitable for dyeing, at least one oxidation dye and at least one amphoteric polymer comprising a repetition of:
   (i) from 45 mol % to 60 mol % of at least one unit derived from a monomer of acrylamide type, (ii) at least one unit derived from a monomer of dialkyldiallylammonium halide type, and (iii) at least one unit derived from a monomer of vinylcarboxylic acid type, wherein the mole ratio of the amount of the at least one unit derived from a monomer of dialkyldiallylammonium halide type to the amount of the at least one unit derived from a monomer of vinylcarboxylic acid type is greater than or equal to 1.

2. The composition according to claim 1, wherein the at least one unit derived from a monomer of acrylamide type is chosen from units of formula (I):

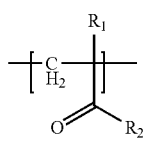

(I)

in which:

$R_1$ is H or $CH_3$, $R_2$ is chosen from amino, dimethylamino, tert-butylamino, dodecylamino and —NH—$CH_2OH$ radicals.

3. The composition according to claim 2, wherein $R_1$ is H and $R_2$ is an amino radical.

4. The composition according to claim 1, wherein the at least one unit derived from a monomer of dialkyldiallylammonium halide type is chosen from units of formula (II):

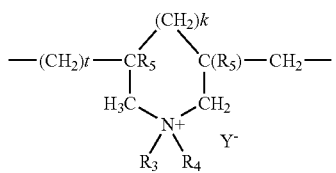

(II)

in which:

k and t are equal to 0 or 1, the sum k+t being equal to 1;

$R_5$ is H or $CH_3$;

$R_3$ and $R_4$, independently of each other, are chosen from independently of one another, $C_1$-$C_4$ alkyl groups, hydroxy($C_1$-$C_5$)alkyl groups, and amido($C_1$-$C_4$)alkyl groups, or $R_3$ and $R_4$ may form, jointly with the nitrogen atom to which they are attached, heterocyclic groups;

$Y^-$ is a bromide, chloride, acetate, borate, citrate, tartrate, bisulfate, bisulfite, sulfate or phosphate anion.

5. The composition according to claim 4, wherein $R_5$ is H, $R_3$ and $R_4$ are methyl radicals, and $Y^-$ is a chloride anion.

6. The composition according to claim 1, wherein the at least one unit derived from a monomer of vinylcarboxylic acid type is chosen from the units of formula (III):

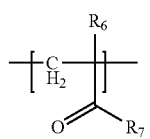

(III)

in which:

$R_6$ is H or $CH_3$, and $R_7$ is a hydroxyl radical or a radical —NH—C($CH_3$)$_2$—$CH_2$—$SO_3H$.

7. The composition according to claim 6, wherein $R_6$ is a hydrogen atom and $R_7$ is a hydroxyl radical.

8. The composition according to claim 1, wherein the at least one amphoteric polymer comprises from 45 mol % to 55 mol % of at least one unit derived from a monomer of acrylamide type.

9. The composition according to claim 1, wherein the at least one amphoteric polymer comprises 30 mol % or less of at least one unit derived from a monomer of vinylcarboxylic acid type.

10. The composition according to claim 1, wherein, in the at least one amphoteric polymer, the mole ratio of the amount of the at least one unit derived from a monomer of dialkyldiallylammonium halide type to the amount of the at least one unit derived from a monomer of vinylcarboxylic acid type ranges from 1 to 2.

11. The composition according to claim 1, wherein the at least one amphoteric polymer comprises at least 25 mol % of at least one unit derived from a monomer of dialkyldiallylammonium halide type.

12. The composition according to claim 1, wherein the at least one amphoteric polymer is chosen from acrylamide/dimethyldiallylammonium chloride/acrylic acid terpolymers.

13. The composition according to claim 1, wherein the at least one amphoteric polymer is present in an amount ranging from 0.1% to 10% by weight relative to the total weight of the composition.

14. The composition according to claim 1, wherein the at least one oxidation dye is chosen from oxidation bases and couplers.

15. The composition according to claim 14, wherein the at least one oxidation base is chosen from ortho- and para-phenylenediamines, double bases, ortho- and para-aminophenols, heterocyclic bases, and the acid addition salts thereof.

16. The composition according to claim 14, comprising a total amount of oxidation base ranging from 0.0005% to 12% by weight relative to the total weight of the composition.

17. The composition according to claim 14, wherein the at least one coupler is chosen from meta-aminophenols, meta-phenylenediamines, meta-diphenols, naphthols, heterocyclic couplers, and the acid addition salts thereof.

18. The composition according to claim 14, wherein the total amount of coupler ranges from 0.0001% to 15% by weight relative to the total weight of the composition.

19. The composition according to claim 1, further comprising at least one oxidizing agent.

20. The composition according to claim 19, wherein the at least one oxidizing agent is chosen from hydrogen peroxide, urea peroxide, alkali metal bromates or ferricyanides, persalts, and redox enzymes optionally in the presence of the respective donor or cofactor thereof.

21. A process for dyeing keratin fibers, comprising,
applying to the hair a composition for the oxidation dyeing of keratin fibers, comprising, in a medium that is suitable for dyeing, at least one oxidation dye and at least one amphoteric polymer comprising a repetition of:

(i) from 45 mol % to 60 mol % of at least one unit derived from a monomer of acrylamide type, (ii) at least one unit derived from a monomer of dialkyldiallylammonium halide type, and (iii) at least one unit derived from a monomer of vinylcarboxylic acid type, wherein the mole ratio of the amount of the at least one unit derived from a monomer of dialkyldiallylammonium halide type to the amount of the at least one unit derived from a monomer of vinylcarboxylic acid type is greater than or equal to 1, wherein the composition is applied to the keratin fibers in the presence of an oxidizing agent; and leaving the composition on the keratinous fibers for a time sufficient to develop the desired coloration.

22. A multi-compartment device comprising at least one first compartment comprising a composition for the oxidation dyeing of keratin fibers, comprising, in a medium that is suitable for dyeing, at least one oxidation dye and at least one amphoteric polymer comprising a repetition of:
  (i) from 45 mol % to 60 mol % of at least one unit derived from a monomer of acrylamide type,
  (ii) at least one unit derived from a monomer of dialkyldiallylammonium halide type, and
  (iii) at least one unit derived from a monomer of vinylcarboxylic acid type, wherein the mole ratio of the amount of the at least one unit derived from a monomer of dialkyldiallylammonium halide type to the amount of the at least one unit derived from a monomer of vinylcarboxylic acid type is greater than or equal to 1; and at least one second compartment comprising at least one oxidizing agent.

23. A method for reducing static electricity at the surface of hair treated with oxidation dyeing, comprising, applying to the hair a composition for the oxidation dyeing of keratin fibers, comprising, in a medium that is suitable for dyeing, at least one oxidation dye and at least one amphoteric polymer comprising a repetition of:
  (i) from 45 mol % to 60 mol % of at least one unit derived from a monomer of acrylamide type,
  (ii) at least one unit derived from a monomer of dialkyldiallylammonium halide type, and
  (iii) at least one unit derived from a monomer of vinylcarboxylic acid type, wherein the mole ratio of the amount of the at least one unit derived from a monomer of dialkyldiallylammonium halide type to the amount of the at least one unit derived from a monomer of vinylcarboxylic acid type is greater than or equal to 1.

* * * * *